US012220663B2

(12) United States Patent
Schraven et al.

(10) Patent No.: US 12,220,663 B2
(45) Date of Patent: Feb. 11, 2025

(54) TUBULAR FIBER MEMBRANE FOR MATERIAL EXCHANGE AND METHOD OF MAKING SAME

(71) Applicant: RHEINISCH-WESTFÄLISCHE TECHNISCHE HOCHSCHULE (RWTH) AACHEN, Aachen (DE)

(72) Inventors: Lotte Schraven, Aachen (DE); Jutta Arens, Aachen (DE); Thomas Schmitz-Rode, Aachen (DE); Ulrich Steinseifer, Hauset (DE); Georg Wagner, Aachen (DE); Peter Christian Schlanstein, Aachen (DE); Andreas Kaesler, Aachen (DE); Felix Hesselmann, Aachen (DE)

(73) Assignee: RHEINISCH-WESTFAELISCHE TECHNISCHE HOCHSCHULE, Aachen (DE)

( * ) Notice: Subject to any disclaimer, the term of this patent is extended or adjusted under 35 U.S.C. 154(b) by 815 days.

(21) Appl. No.: 17/257,903

(22) PCT Filed: Jul. 30, 2019

(86) PCT No.: PCT/EP2019/070436
§ 371 (c)(1),
(2) Date: Jan. 28, 2021

(87) PCT Pub. No.: WO2020/025581
PCT Pub. Date: Feb. 6, 2020

(65) Prior Publication Data
US 2021/0268443 A1 Sep. 2, 2021

(30) Foreign Application Priority Data

Jul. 30, 2018 (DE) .......................... 102018005937.6

(51) Int. Cl.
B01D 63/02 (2006.01)
A61M 1/16 (2006.01)
(Continued)

(52) U.S. Cl.
CPC ........... B01D 63/025 (2013.01); B01D 63/04 (2013.01); B01D 69/08 (2013.01); B01D 71/00 (2013.01);
(Continued)

(58) Field of Classification Search
CPC ...... B01D 63/025; B01D 63/04; B01D 69/08; B01D 71/00; B01D 2313/042;
(Continued)

(56) References Cited

U.S. PATENT DOCUMENTS 4,902,476 A 2/1990 Gordon et al.
4,975,247 A 12/1990 Badolato et al.
(Continued)

FOREIGN PATENT DOCUMENTS

DE 19711083 A 9/1998

Primary Examiner — Pranav N Patel
(74) Attorney, Agent, or Firm — Andrew Wilford

(57) ABSTRACT

The invention relates to a method for producing a device for material exchange between two mediums, in which at least one mat of semipermeable hollow fibres (3) is wound onto a winding core (2), which has at least one core opening (2a) in its outer surface for a first in- or out-flowing medium, and the winding core (2) is arranged in an axially extending housing (1) having at least one housing opening (1a) for the first in- or out-flowing medium, and the axial end regions of the housing (1) are sealed by an adhesive (4) arranged around the hollow fibres (3), wherein at least one chamber region (5) surrounding the hollow fibres (3) is formed via the adhesion between the axial end regions (1b, 1c) of the housing (1) and between the winding core (2) and the housing (1), through which chamber region the first medium
(Continued)

can flow via the core opening (2*a*) and the housing opening (1*a*), wherein the axial distance between the core opening (2*a*) and the housing opening (1*a*) is adjusted to a desired value of multiple possible values via the axial shifting of the winding core (2) relative to the hollow fibre winding (3) arranged around the winding core (2) and relative to the housing (1), and the hollow fibres (3) are adhered to the side of the housing (1) near to the housing opening (1*a*) in a region between the axial end surface of the housing and the housing opening (1*a*), and the hollow fibres (3) are adhered to the side of the housing (1) near to the core opening (2*a*) in a region between the axial end surface of the housing and the core opening (2*a*). The invention also relates to a number of multiple devices for material exchange between two mediums, wherein all devices comprise at least identical housings (1) and winding cores (2) that are identical at least in regions.

6 Claims, 4 Drawing Sheets

(51) Int. Cl.
*B01D 63/04* (2006.01)
*B01D 69/08* (2006.01)
*B01D 71/00* (2006.01)

(52) U.S. Cl.
CPC ..... *A61M 1/1621* (2014.02); *B01D 2313/042* (2022.08); *B01D 2313/08* (2013.01); *B01D 2313/21* (2013.01)

(58) Field of Classification Search
CPC ............ B01D 2313/08; B01D 2313/21; B01D 63/0222; A61M 1/1621; A61M 1/1698
See application file for complete search history.

(56) References Cited

U.S. PATENT DOCUMENTS

| | | |
|---|---|---|
| 5,263,982 A * | 11/1993 | Shimomura ......... B01D 63/021 623/23.65 |
| 6,004,511 A | 12/1999 | Biscegli |
| 8,757,807 B1 | 6/2014 | Disley |
| 9,761,163 B2 | 9/2017 | Ohyama et al. |
| 10,955,195 B2 | 3/2021 | Stoecker |
| 2002/0093565 A1 | 7/2002 | Watkins |
| 2004/0046899 A1 | 3/2004 | Bonnett |
| 2017/0164449 A1 | 6/2017 | Schimizu |
| 2018/0207344 A1 | 7/2018 | Hisamatsu et al. |
| 2020/0122089 A1* | 4/2020 | Ritter .................. A61M 1/1621 |

* cited by examiner

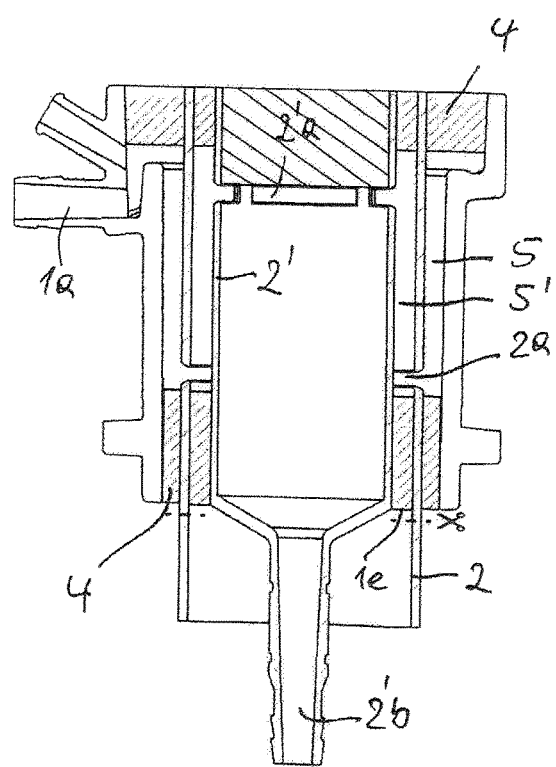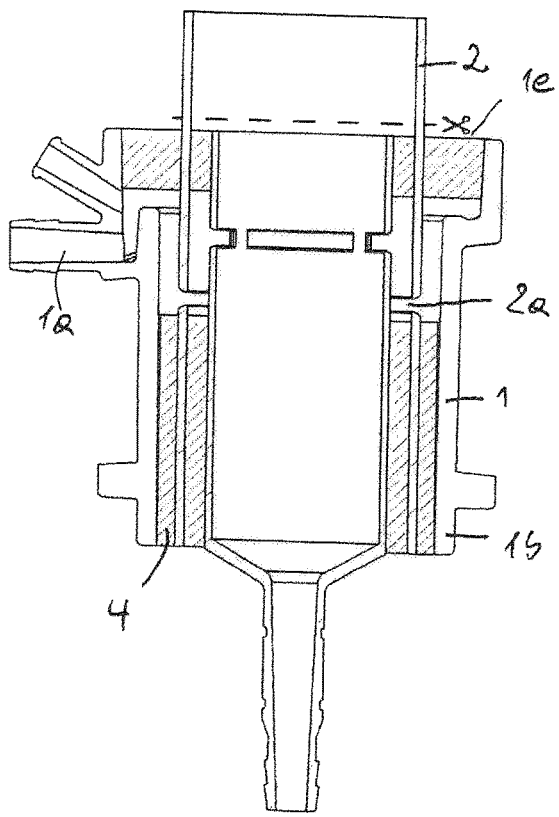
Fig. 5
Fig. 6

TUBULAR FIBER MEMBRANE FOR MATERIAL EXCHANGE AND METHOD OF MAKING SAME

CROSS REFERENCE TO RELATED APPLICATIONS

This application is the US-national stage of PCT application PCT/EP2019/070436 filed 30 Jul. 2019 and claiming the priority of German patent application 102018005937.6 itself filed 30 Jul. 2018.

FIELD OF THE INVENTION

The invention relates to a method of making an apparatus for exchanging substances between two media.

BACKGROUND OF THE INVENTION

Such an apparatus has a winding core that in turn has an outer surface formed with at least one core opening for a first medium flowing in or out and is wound with at least one mat of semipermeable fiber tubes. The winding core is in an axially elongated housing, preferably coaxially, at least one port being provided for a first outflowing medium, and the axial ends of the housing sealed with an adhesive around the fiber tubes, especially at the axial ends of the housing with an adhesive that fixes the wound fiber tubes to the core, to each other and to the housing and for sealing between the axial ends of the housing and between the winding core and the housing at least a chamber area surrounding the fiber tubes is formed which is traversed between the core opening and the port by the first medium. The method also preferably includes the step that the fiber tubes in their extension between the axial ends of the housing are flowed through in their interiors by the second medium. Possibly the axial ends of the fiber tubes after sealing are freed of the adhesive, e.g. by cutting.

Processes of this type are generally known for making apparatuses for mass transfer in the prior art. Such apparatuses are usually used for mass transfer between two media and serve to reduce unwanted substances in blood and if necessary to enrich the desired substances.

Apparatuses for mass transfer, typically oxygenators, are used to strip of carbon dioxide and enrich it with oxygen. Such apparatuses can also be used as dialyzers for mass transfer.

The first fluid flowing through the chamber area formed medium is in these applications, especially in the application as oxygenator, is usually blood, and the gas, normally oxygen, flows through the semipermeable fiber tubes.

In a typical application, the core opening in the winding core outputs the medium out of the core to engage the winding of fiber tubes wound on the core. The at least one core opening usually opens into an inner tubular area of the core and connects it to the blood supply. The inner tubular area opens into a hose connection.

The term semipermeable fiber tube is used in this context invention to mean a fiber tube that allows material to move between the interior of the fiber tube and the outside for the desired mass transfer. In essence, then, a semipermeable fiber tube is permeable to one of the two media, especially gas, in the oxygenator application oxygen and carbon dioxide, and not permeable, so impermeable, to the other medium, in the one mentioned application for blood. Such semipermeable fiber tubes can be made of silicone, polypropylene (PP) or polymethylpentene (PMP). The mass transfer usually takes place as diffusion through the fiber tube material. It is also possible to use a convective mass transfer if the semi-permeable fiber tubes have pores that are traversable by for one medium and but not for the other medium. For example, such porous fiber tubes are used whose pore diameters are less than 200 nm.

The type of semipermeable fiber tubes actually used can be different when used for mass transfer depending on the application of the apparatus.

In the prior art it is known that treatment of different groups of people requires differently sized apparatuses for exchanging substances. Under different sized apparatuses is essentially understood, that these apparatuses differ in size of mass transfer surfaces and/or are of different volumes. For example, for infants such apparatuses are used that have significantly smaller mass transfer surfaces and smaller volumes than comparable apparatuses for adults or children. In the prior art there are at least three different sizes of such apparatuses for treatment to keep in stock, namely a size for adults, a size for children, and a size for babies.

This implies that correspondingly different sized apparatuses must be manufactured and stocked, which entails increased manufacturing and storage costs. Similarly the manufacturer needs different tools to make the different to be able to make different sizes.

OBJECT OF THE INVENTION

It is therefore an object of the invention to provide a method of making apparatuses for mass transfer of the above-described generic type, by means of which it is possible to produce apparatuses of different sizes inexpensively, preferably when using at least identical housings and identical winding cores to produce the required differently sized mass transfer areas or internal volumes.

SUMMARY OF THE INVENTION

This object is achieved according to the invention in that the method allows axial displacement of the winding core relative to the fiber tube winding wrapped around the winding core and thus adjustment of the axial spacing in the housing between the core opening and the port to a desired value of several possible values and the fiber tubes are sealed to the end of the housing close to the port between the axial face of the housing and the port and to the side of the housing near the core opening, the fiber tubes being sealed in one area between the axial face of the housing and the core opening, in particular axially sealed by the core opening.

With the above-described axial displacement of the winding core for setting a desired axial position of the core opening and thus to achieve a desired spacing between the core opening and the port preferably, while, during moving the winding core, the fiber tube winding remains axially stationary relative to the housing.

According to the invention, an essential core idea is that with a set of identical housings and a set of identical winding cores due to the different displacement of the winding cores and thus differently set positions of the core openings several apparatuses for mass transfer between two media can be made from at least originally identical components, creating different large effective mass transfer surfaces and/or different large internal volumes.

These effective mass transfer surfaces of different sizes and/or volumes are achieved by varying the axial spacing between the core opening and the port, thus the axial length of the chamber area through which the fluid flows, despite use of identical components of the apparatuses. There are therefore, as it were, different axial lengths of the fiber tubes contacted by the medium in the chamber, such as for example blood, especially when the areas beyond the housing or core opening, viewed from inside the apparatus in the direction of housing end face, are axially blocked by the above-described adhesive.

For this purpose, the invention preferably provides, as described above that at one end of the housing, which is close to the core opening, the adhesive preferably is used with such an amount intended for potting at this end that is sufficient to allow adhesion axially up to the core opening.

This is essentially supposed to mean that the amount of adhesive is dimensioned in such a way that the core opening remains open, in that the position of the adhesive surface below the axial position of the core opening is set back axially.

The spacing between the adhesive surface and the core opening axially is fundamentally irrelevant. Preferably, however, a spacing is provided in the range from 1% to 10% of the spacing between the core opening and the nearby axial end face of the housing.

The method according to the invention can thus achieve that by moving the core opening of the winding core in one direction further into the interior of the housing into and by using a larger amount of adhesive a smaller mass transfer surface and a smaller internal chamber volume of the apparatus can be achieved, as compared to the axial position shifted further to the end face the core opening and a smaller amount of adhesive.

The invention can provide that there are two spaced maximum axial positions between which the core opening can be positioned by moving the winding core within the housing, all the positions between these maximum positions potting being working positions that determine the size of the mass transfer area and/or volume. The farther the core opening is shifted from the axial face of the housing toward the interior of the housing, the more adhesive is used for bonding.

The method according to the invention thus has the great advantage that for the provision of apparatuses of different sizes of mass transfer surface or volumes no size-specific tools and manufacturing processes are required; instead these different sizes can be made with the same tools and identical housings and winding cores.

The method according to the invention is achieved by the arrangement of the winding core in the housing of the described chamber that is between the winding core and the housing and is at least substantially filled with the fiber tube winding. Only one winding core is used, a chamber is provided in which the medium can flow between the core opening and the port.

In a further development, the invention can also provide that with the method according to the invention an apparatus is made with two or more nested winding cores, on one of which a fiber tube winding is wound, so that there is also at least one fiber tube winding between two cores. Thus accordingly, several nested chamber areas are provided between which the medium can flow, namely in particular through the core openings in the flow direction through the winding cores.

Thus a single or multiple reversal of flow direction is produced according to the invention apparatuses. In particular, the invention can also provide different types of fiber tubes in the different chambers between two winding cores or between a winding core and the housing.

In a method of manufacture according to the invention, it can for example be provided that in the above-described winding core at least one further winding core with one core opening is arranged for medium flowing in or out, its wound fiber tubes thus being between these two winding cores, whereby axial displacement at least one winding core, preferably at least the outer winding core and possibly also of the other winding core, sets the axial spacing between the core openings of the winding cores lying one inside the other to a desired value of several possible values. So there is therefore the possibility of axial displacement, e.g. of the outer winding core, to vary the axial chamber length, in particular the chamber length resulting therefrom after the sealing process, between this core and the housing wall, as well as influencing the axial chamber length, of that chamber that is between the nested cores is formed.

The invention can provide in a development that the winding core, in particular the only winding core, or at least one of several winding cores, has an axial length that is greater than the axial length of the housing. This ensures that the core opening of such a winding core can be moved arbitrarily between two maximally possible axial end positions, in any of these possible intermediate positions radially covering the winding core with the housing there, so that sealing with adhesive in any of the possible positions of the core opening can be carried out. With an axial length of the winding core selected in this way it can then happen that, after movement to set the desired axial position of the core opening, the winding core projects at least at one end of the winding core past one axial end face of the housing.

If this projection is less than the axial inner free length of an end cap of the housing there is essentially no need to take further steps since in such a case the end cap can easily be fitted on the axial end of the housing and can be connected to it, for example by screw.

However, if the excess area is too long, especially longer than an inner free axial length of a housing end cap, according to the invention this excess end part is cut off after potting, especially near the axial end face and then an axial end cap can cover the projecting part and potted.

There is also alternatively or cumulatively to the above steps the possibility that an axial housing end cap having a throughgoing hole can be fitted with this hole over the projecting end part of the winding core and with potted with the axial end of the housing, in particular also with the remaining part.

It is particularly preferred for the invention procedure to close the axial ends of the housing with identical axial housing end caps.

The invention preferably provides that the winding core at least at one end always projects axially past one of the axial end faces of the housing, preferably namely with such an axial end part of the winding core for connecting a hose to feed the medium into the interior of the winding core. Such an end part can e.g. be tapered in diameter compared to otherwise, especially with a predominant axial length into the remaining area of the winding core in the housing area.

The invention can provide that the identical housing end caps each have a throughgoing hole, and at least one of the end caps fits with its concavity over the projecting end part of the winding core, namely preferably at least one the projecting end part through which the medium is supplied while the hole in the other end cap is plugged with a closure element. This ensures that all the end caps to be used for the manufacture of an apparatus can basically be designed identically.

The invention thus achieves a particular advantage that a set of multiple apparatuses for substance exchange between two media cam be made with the inventive processes, with all the apparatuses at least having identical housings and at least in certain areas identical winding cores. The winding cores are in the sense the invention at least partially identical, since they are originally exactly identical and, if applicable, within the scope of the manufacturing process can be cut down. Thus both are then used to make apparatuses with identical winding cores, disregarding cut-off portions. Preferably it can be provided that the windings of fiber tubes are identical.

In such an number of apparatuses however, by moving the core openings of the winding cores during the manufacturing processes into different axial positions, so in conjunction with different amounts of adhesive in the apparatuses one attains differently sized effective mass transfer surfaces and/or volumes.

BRIEF DESCRIPTION OF THE DRAWING

Embodiments of the invention, in particular those with apparatuses manufactured according to the method according to the invention are described in more detail with reference to the figures discussed below in which:

FIG. 1-6 are axial sections through variants of the instant invention; and

SPECIFIC DESCRIPTION OF THE INVENTION

Figure 1:
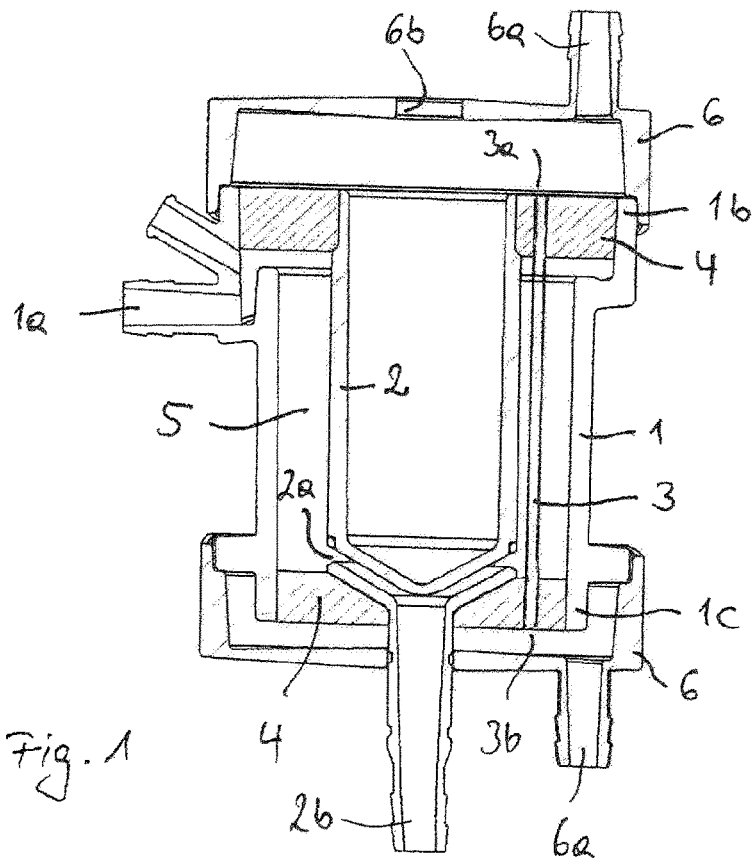

FIG. 1 shows an apparatus manufactured according to the invention apparatus for example for exchanging substances between blood and a gas, in particular for oxygenating blood. FIG. 1 shows an axially elongated housing 1 with a port 1a. This port 1a in this embodiment extends radially as a tubular hose-connection fitting from housing 1.

A winding core 2 is inserted into the housing 1, here in particular coaxial to the housing 1, and has a core opening 2a. This core opening 2a is an annular gap connected to a hose-connection fitting 2b. The winding core 2 is surrounded by a fiber mat formed by a plurality of joined fiber tubes 3, but in this view only a single fiber tube 3 is shown schematically for clarity. This fiber tube 3 also is, for the sake of clarity, enlarged and shown at a slight spacing from the core.

At each of axial ends 1b and 1c of the housing 1 the fiber tubes 3 are potted in an adhesive body 4 that also bonds them to the winding core 2 and to the housing 1. The ends 1b and 1c of the housing 1 are therefore sealed to contain the contents of a chamber 5 from the outside.

This bonding, which is also called potting in the art, is for example carried out in a centrifuge so that centrifugal forces restrict the adhesive to the axial ends of the housing. The potting or bonding of the fiber tubes 3 takes place in such a centrifuge for the axial ends 1b and 1c accordingly one after the other, with the end being bonded radially outward of the centrifuge axis.

Manufacture of this type produces the inner chamber 5 that is delimited axially between the potted ends 1b and 1c and radially between the outer surface of the winding core 2 and the inner wall surface of the housing 1. This chamber 5 therefore contains the semipermeable fiber tubes 3 around which the medium flows. It can be seen here that medium supplied through the hose-connection fitting 2b of the winding core can enter the chamber 5 via the core opening 2a and then flow s all around all of the fiber tubes of the winding on the outside and after flowing axially through the chamber region 5 exits through the port 1a. The direction of flow is here for example from the chamber opening 2a to the port 1a and can be reversed.

The axial end of each semipermeable fiber tube 3, namely the ends 3a and 3b, are accessible, and a second medium flows axially through the fiber tubes 3, for example in the application as an oxygenator by a gas. This gas can be pumped via an appropriate connection 6a in one of two axial end caps 6 into and out of the interior fiber tubes 3.

If necessary, the axial end faces 3a, 3b of the fiber tubes 3 are cleared if they get clogged by during potting.

The axial end caps 6 shown here are identical and each have a central hole 6b plugged in the upper cap of the figure, but here is shown in the open state, and that of the lower end cap 6 the winding core 2 is fitted with a tapered hose connection 2b. In this way, identical axial housing end caps 6 are used, with the unused hole 6b of only one of the end caps closed with an unillustrated plug.

FIG. 1 shows that the axial spacing between the core opening 2a and the port 1a, which axially flow is through and which is defined by the length of the chamber area 5 and by the axial length of the fiber tubes 3, so as to define, as it were, the total immersed surface of the fiber tubes 3 that participates in mass transfer.

Figure 2:
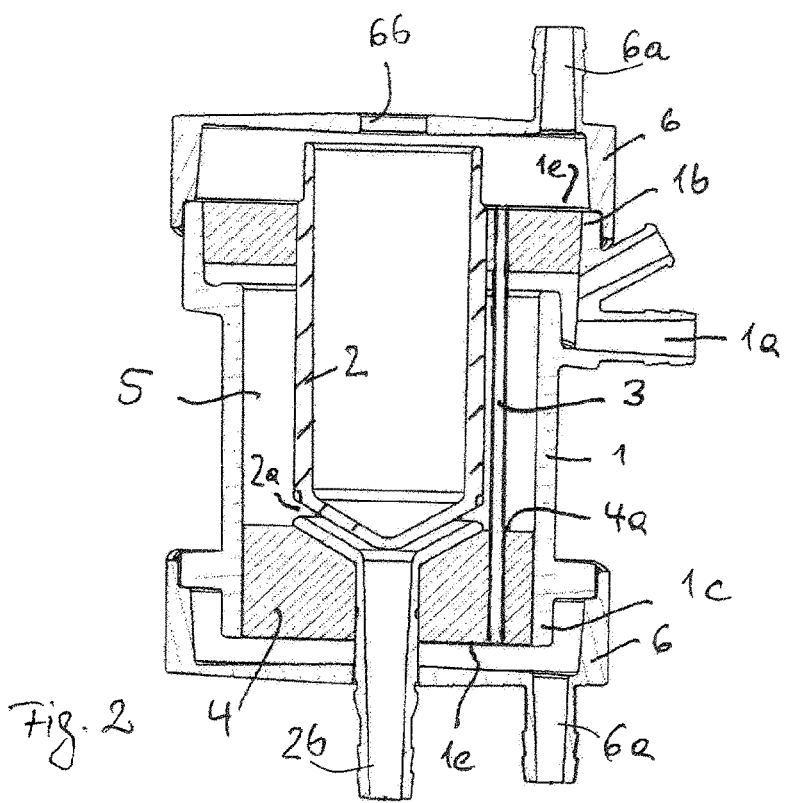

FIG. 2 shows an apparatus according to the invention apparatus that, like the apparatus of FIG. 1, has exactly the same components, i.e. housing, winding core, fiber tubes and end caps.

Unlike FIG. 1, however, the core is shifted during manufacturing according to the invention, to axially move the core opening 2a, because here before potting the core 2 is shifted axially in FIG. 2, thereby moving the core opening 2a upward further into the interior of the housing 1 in comparison to FIG. 1.

Moving the core opening 2a further into the housing 1 creates a shorter axial spacing between the core opening 2a and the port 1a and accordingly also a smaller axial length for flow around the winding formed by the fiber tubes 3.

In the manufacture method according to the invention, the manufacture of the apparatus according to FIG. 2 uses more adhesive 4 to get a greater fill height at the lower axial end 1c of the apparatus. As in FIG. 1, in FIG. 2 the amount of adhesive 4 to be used when sealing the fiber tubes at the lower end 1c of the housing moves the surface 4a of the adhesive axially upward in the housing 1 to raise the core opening 2a without plugging the core opening 2a with adhesive.

The invention can provide between the surface 4a of the adhesive 4 and the lower edge of the core opening 2a an axial safety spacing, such as 1% to 10% of the spacing between the core opening 2a and the lower end face of the end 1c.

It can be clearly recognized by the hatching of the adhesive 4 in FIG. 2 compared to the adhesive 4 in FIG. 1 that the fill height and thus the fill quantity of the adhesive 4 in the embodiment according to FIG. 2 is greater than in FIG. 1.

In both cases from inside the chamber 5 viewed areas beyond the core opening 2a the adhesive 4 is excluded from the chamber area 5. Consequently both the chamber volume of the chamber 5 in FIG. 2 is smaller than in FIG. 1 as well as the actively active area of the fiber tubes that take part in mass transfer.

It can be seen here that in FIG. 2 unlike in FIG. 1 the winding core 2 projects axially above the upper end face 1e of the upper end 1b. However, the axial projection above the end face 1*e* is less here than the inner free axial length of the end cap 6, so that the projecting end of the winding core 2 is completely covered by the end cap 6.

It can therefore be seen from FIGS. 1 and 2 in comparison that through the simple axial shifting the position of the core opening 2*a* and changing the amount of adhesive 4 near this core opening 2*a* allows systems with different volumes and the exchange areas to be made with identical components.

Figure 3:
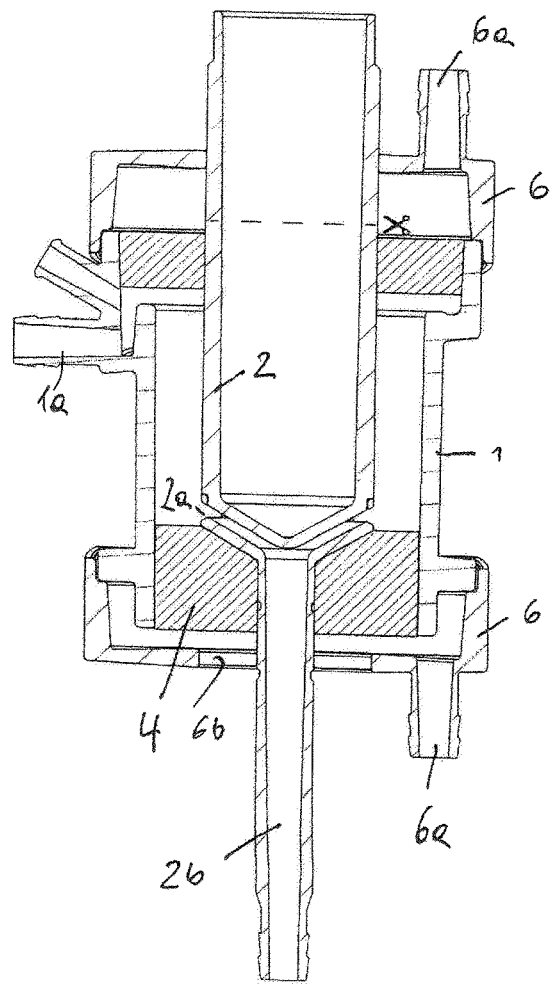

FIG. 3 shows another embodiment of the method or of the apparatus where the winding core 2 compared to the embodiment in FIGS. 1 and 2 is of significantly increased axial length. This ensures that the core opening 2*a* in FIG. 3 is shifted clearly closer to the port 1*a* during before sealing and thus provides even significantly smaller sizes for the internal volume of the chamber 5 or in the case of the active mass transfer surface.

In FIGS. 3 to 6, the fiber tubes are not shown, but also here surround the respective core, as in FIGS. 1 and 2.

Figure 4:
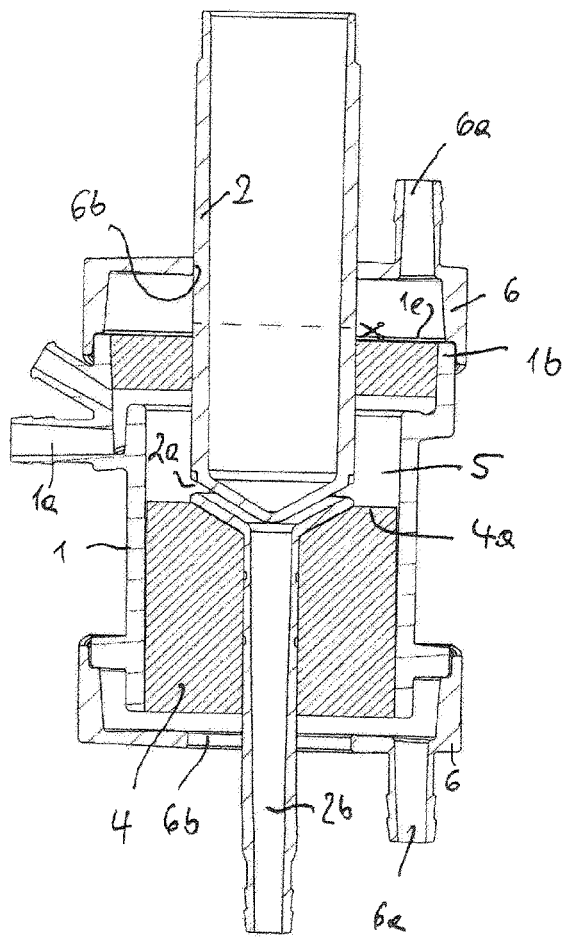

Here, too, it can be seen in the comparative consideration of FIGS. 3 and 4 that in FIG. 4 the amount of adhesive 4 is greater due to the higher axial position of the core opening 2*a* than in FIG. 3. In both figures the surface 4*a* of the facing the interior of the chamber 5 adhesive is raised to the lower edge of the core opening 2*a*, in particular, however, without the adhesive in the sealing process getting into the core opening 2*a*. Again, a safety spacing as described at the beginning must be observed.

Because of the significantly increased axial length of the winding core 2 provided at least the projecting axial upper end 1*b* of the winding core 2 projecting from the housing 1 can be cut off before a lid 6 is put on, as indicated schematically by the scissors on the dashed line symbolically above the axial end face 1*e* of the housing 1.

Alternatively, however, the invention can also provide that, in use of the housing, end caps 6 with holes 6*b* large enough to cover the area of winding core 2 surround and are sealed thereon, so cutting off is not absolutely necessary so that here FIGS. 3 and 4 also show the axially upper winding core area can projects upward from the end cap 6 through the opening 6*b*. The invention can provide here that in the hole 6*b* at the lower end, where this hole is in cross section, it surrounds the narrowed hose connection area 2*b* of the winding core 2 with an additional sealing element.

FIG. 5 shows a further variant of the method according to the invention in which two nested cores are used. In this embodiment, the here radially outer winding core 2 has its radial essentially ring-shaped core opening 2*a* pointing outward and that core, which in the context of the inventive method is shifted axially, defines the length of the chamber area 5. Here, too, the adhesive is 4 is brought up to the lower edge of the core opening 2*a*, so that essentially the axial length of the outer chamber 5 is defined by the spacing between the opposite and one another assigned surfaces of the adhesive 4 or the axial spacing between the core opening 2*a* and the port 1*a*.

A further core 2' is provided within the core 2, also surrounded by an unillustrated winding of fiber tubes, this core having a core opening 2'*a* that is axially spaced from the core opening 2*a* and that preferably is in this embodiment essentially axially level with the port 1*a*.

The winding core 2' here essentially corresponds to the embodiments of the winding core 2 of FIGS. 1 and 2, apart from the position of the core opening.

The method according to the invention here proposes, when comparing the embodiments of FIGS. 5 and 6, that during manufacture the axial position of the inner winding core 2', as in the various embodiments of FIGS. 5 and 6, is unchanged, whereas the axial position of the outer winding core 2 in FIG. 6 with respect to FIG. 5 is shifted such that the core opening 2*a* of the outer core 2 in FIG. 6 is closer to the port 1*a* than in FIG. 5.

This is achieved in that in the case of the procedure as described for the other figures the core 2 with its core opening 2*a* is pushed further into the housing and then in FIG. 6 more adhesive is used to attach the fiber tubes to the lower axial end 1*b* of the housing 1 with one another to glue them to the housing and the cores.

In principle, the inner winding core 2' can move between two maximum positions, like the outer winding core 2.

The embodiments of FIGS. 5 and 6 result form two radially nested chamber areas 5 and 5', the one after the other in the direction of flow from the supplied medium flow through, whereby in these chamber areas 5 and 5' there are identical or different fiber tubes.

The flow path here will essentially be such that the medium enters through the inlet hose connection 2'*b* of the inner winding core 2' and moves from its core opening 2'*a* into the inner chamber area 5', thus into the interior of the core 2, from whose core opening 2*a* it flows out into the outer chamber area 5 and flows from there to the outlet port 1*a*.

By shifting the core opening 2*a* of the outer core when performing the method according to the invention, bonding is achieved in that the spacing between the core openings 2*a* and 2'*a* of outer and inner cores can be set variably, which thus affects the mass transfer surfaces of the fiber tubes in the chambers 5 and 5' has the same effect.

FIG. 5 shows that the winding core 2*a* projects downward past the axial end face 1*e* of the housing 1, so that according to the invention in which the embodiment of FIG. 5 with the higher volume and the larger exchange surface the core 2 is cut to length in its lower area, whereas in the embodiment of FIG. 6 the same external core 2 with its upper axial end projecting up past the axial end face 1*e* of the housing 1 has an upper end that can be cut to length, as shown by the schematic cut line.

The also provided end caps, which are shown in FIGS. 1 to 4 are not shown in FIGS. 5 and 6, but are basically also used to move gas through the fiber tubes. Here too as in the above-described embodiments, the covers either fit with the larger cross-section of the outer winding core or of the inner connection cross-section of the inner winding core can be adjusted.

All figures make it clear that in spite of the manufacture use of identical components, in particular identical housings and winding cores, apparatuses with different volumes and mass transfer areas can be realized simply by moving the core openings with respect to their axial position and use of different amounts of adhesive 4.

Figure 7:
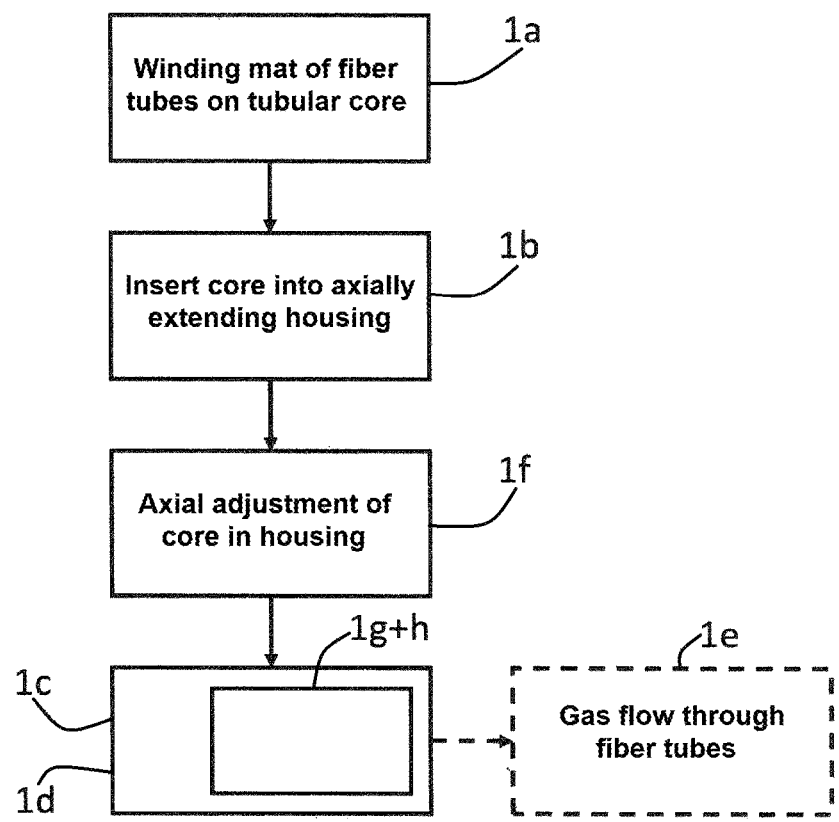
FIG. 7 is a diagram illustrating the method of the invention.

FIG. 7 is a flow diagram for carrying out the method using steps 1*a* to 1*h* of original claim 1.

In first step 1*a*, a mat 2 of fiber tubes is wound around a core 2 with an outer surface forming at least one core opening 2*a* that has a first medium flowing in or out, as shown in FIG. 1.

In following step 1*b*, the winding core 2 is fitted into an axially extending housing, in particular a cylindrical housing 1, preferably arranged coaxially, and having at least one port 1*a* for the inflowing or outflowing medium.

An axial displacement then takes place in step if of the winding core 2 relative the winding core 2 surrounded by the fiber-tube winding 3 and the housing 1, whereby an axial spacing between the core opening 2*a* and the port 1*a* is set to a desired value of several possible values. Two setting modes are shown in FIGS. 1 and 2. In these figures the same winding core 2 has different axial positions relative to the housing 1 and to the fiber tubes 3.

Then in step 1c, the axial ends of the housing 1 are sealed around the fiber tubes 3 with adhesive 4; preference is given to the axial ends 1b, 1c of the housing 1 with adhesive 4 securing the wound fiber tubes 3 with the core 2, one below the other and to the housing 1.

Therefore, in this step 1c, steps 1g and 1h are executed, namely according to step 1g depositing adhesive fat the opening to the housing 1a at the near side of the housing 1 and the fiber tubes 3 and in an area between the axial end face of the housing and the port 1a and, according to step 1h, putting adhesive the side of the housing 1 near the core opening 2a the fiber tubes 3 in an area between the axial end face of the housing and the core opening 2a, in particular axially up to the core opening 2a. The FIGS. 1 and 2 show the final result of the bond for two different axial positions.

According to this, in step 1d adhesive is applied between the axial ends 1b, 1c of the housing 1 and between at least the fiber tubes 3 surrounding chamber region 5 formed between the winding core 2 and the housing 1, so that the core opening 2a and the port 1a can pass the first medium, in particular blood.

Preferably a second medium, in particular a gas, flows through the fiber tubes 3 between the axial ends 1b, 1c of the housing 1.

The invention claimed is:

1. A method of making an apparatus for exchanging substances between first and second mediums, the method comprising the steps of:
    winding a mat of semipermeable fiber tubes on an outer winding core that has an outer core opening for inflow or outflow of the first medium,
    fitting the outer winding core with the mat in an axially extending housing for flow of the first medium into or out of a port of the axially extending housing surrounding the outer winding core and having axially opposite ends,
    axially displacing the outer winding core relative to the fiber tubes around the outer winding core and relative to the housing to adjust an axial spacing between the outer winding core opening and the port to a desired value from several possible values,
    bonding with a sealing adhesive at the axial ends of the housing the tubes to the outer winding core, to one another, and to the housing, and thereby forming a chamber containing the tubes and through which the first medium can flow between the outer winding core opening and the port and for flow of the second medium through the tubes between the axial ends of the housing for substance exchange between the first and second mediums,
    sealing an end of the housing close to the port such that the fiber tubes are sealed with adhesive in an area between one of the axial ends of the housing and the port, and
    sealing and bonding the fiber tubes to another end of the housing close to the outer core opening in an area between an axial end face of the housing and the outer core opening axially up to the outer core opening.

2. The method according to claim 1, further comprising:
    an inner winding core nested in the outer winding core and having an inner core opening for the medium flowing in or out, the fiber tubes extending between the inner and outer winding cores such that axial displacement of at least the outer winding core sets an axial spacing between the inner and outer core openings to a desired value from several possible values.

3. The method according to claim 1, wherein the outer winding core has an axial length that is greater than an axial length of the housing and after movement to adjust an axial position of the outer core opening that projects at least at one end past the axial end face of the housing, the method further comprising the step of, after sealing,
    cutting off excess of the outer winding core near the axial end face and an axial housing end cap, the projecting part extending past and being connected to the axial end of the housing, and/or
    fitting an axial housing end cap formed with a hole over the projecting part and sealing same with one of the axial ends of the housing.

4. The method according to claim 1, further comprising the steps of:
    closing the axial ends of the housing by identical axial housing end caps.

5. The method according to claim 4, wherein the identical housing end caps each have a hole, one of the end caps with the respective hole being fitted over a projecting part of the outer winding core and the hole in the other end cap being plugged with a closure element.

6. The method according to claim 1, comprising the step of:
    using a set of the housings and a set of the outer winding cores for creating different displacements of the outer winding cores and thus several different set positions of the outer core openings for adjusting mass transfer between the first and second mediums across mass transfer surfaces of different sizes.

* * * * *